United States Patent [19]

Hessburg

[11] 4,442,553
[45] Apr. 17, 1984

[54] INTRAOCULAR LENS

[76] Inventor: Philip C. Hessburg, 801 Park La., Grosse Pointe Park, Mich. 48230

[21] Appl. No.: 303,084

[22] Filed: Sep. 17, 1981

[51] Int. Cl.³ .......................... A61F 1/16; A61F 1/24
[52] U.S. Cl. ........................................................ 3/13
[58] Field of Search ........................................ 3/13, 1

[56] References Cited

U.S. PATENT DOCUMENTS

| 4,014,049 | 3/1977 | Richards et al. | 3/13 |
| 4,254,510 | 3/1981 | Tennant | 3/13 |
| 4,257,130 | 3/1981 | Bayers | 3/13 |
| 4,315,337 | 2/1982 | Choyce | 3/13 |
| 4,316,292 | 2/1982 | Alexeev | 3/13 |

FOREIGN PATENT DOCUMENTS 563174  7/1977  U.S.S.R. .................................. 3/13

OTHER PUBLICATIONS

The Leiske Physioflex Style 10 Anterior Chamber Lens Brochure by Surgidev Corp., Santa Barbara, Calif.

*Primary Examiner*—Ronald L. Frinks
*Attorney, Agent, or Firm*—Poms, Smith, Lande & Rose

[57] ABSTRACT

An intraocular lens designed for placement across the anterior chamber of the eye. The lens is of the non-rigid type and comprises a lens body having opposed support haptics of filament material shaped to provide controlled flexibility and wherein the free ends of each haptic loop are disposed in edge bores in the lens body disposed on radius lines passing through the optical center of the lens body which radius lines subtend an angle of from 2° to 10°.

3 Claims, 17 Drawing Figures

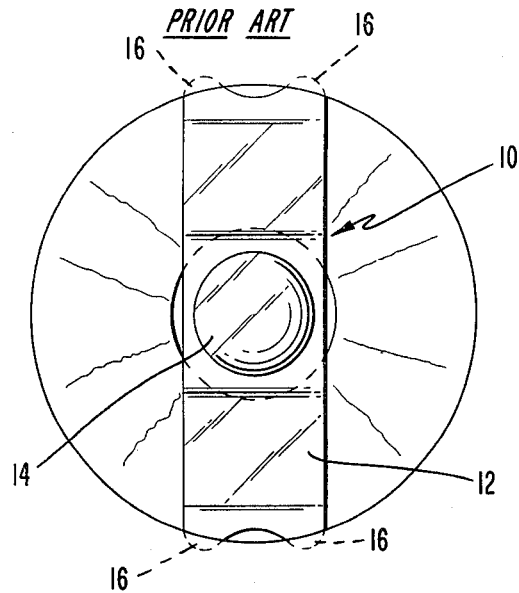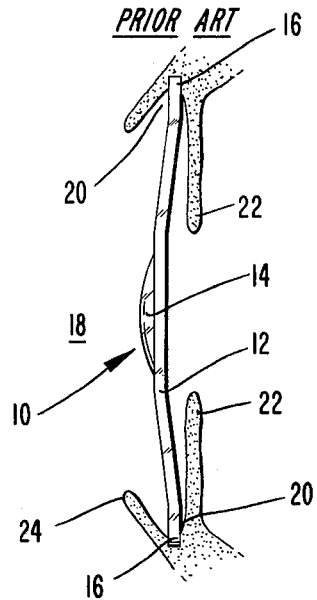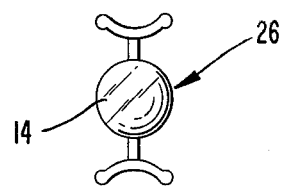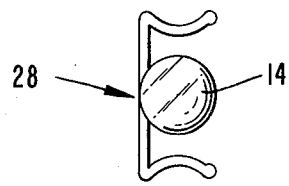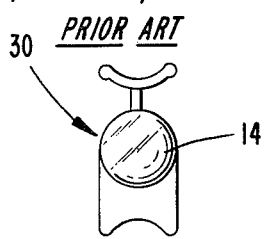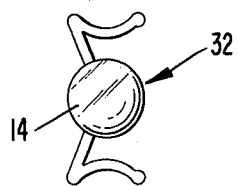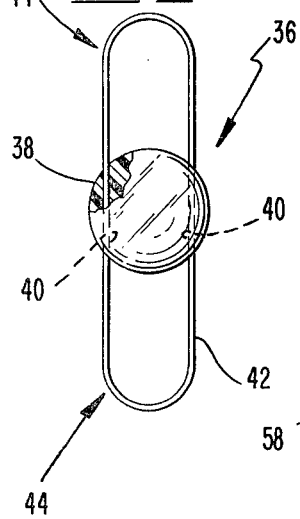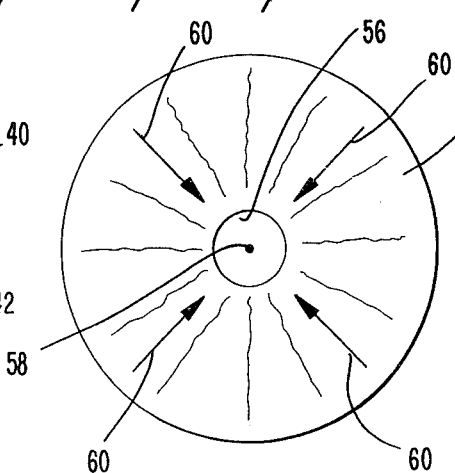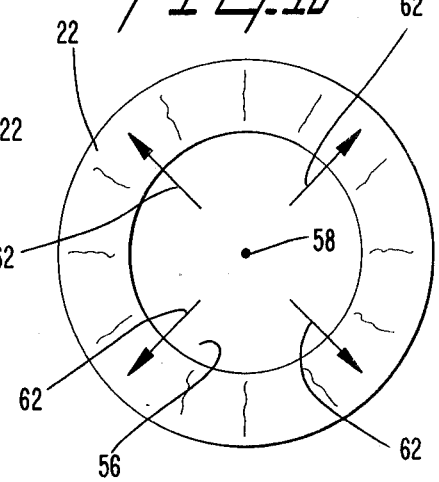

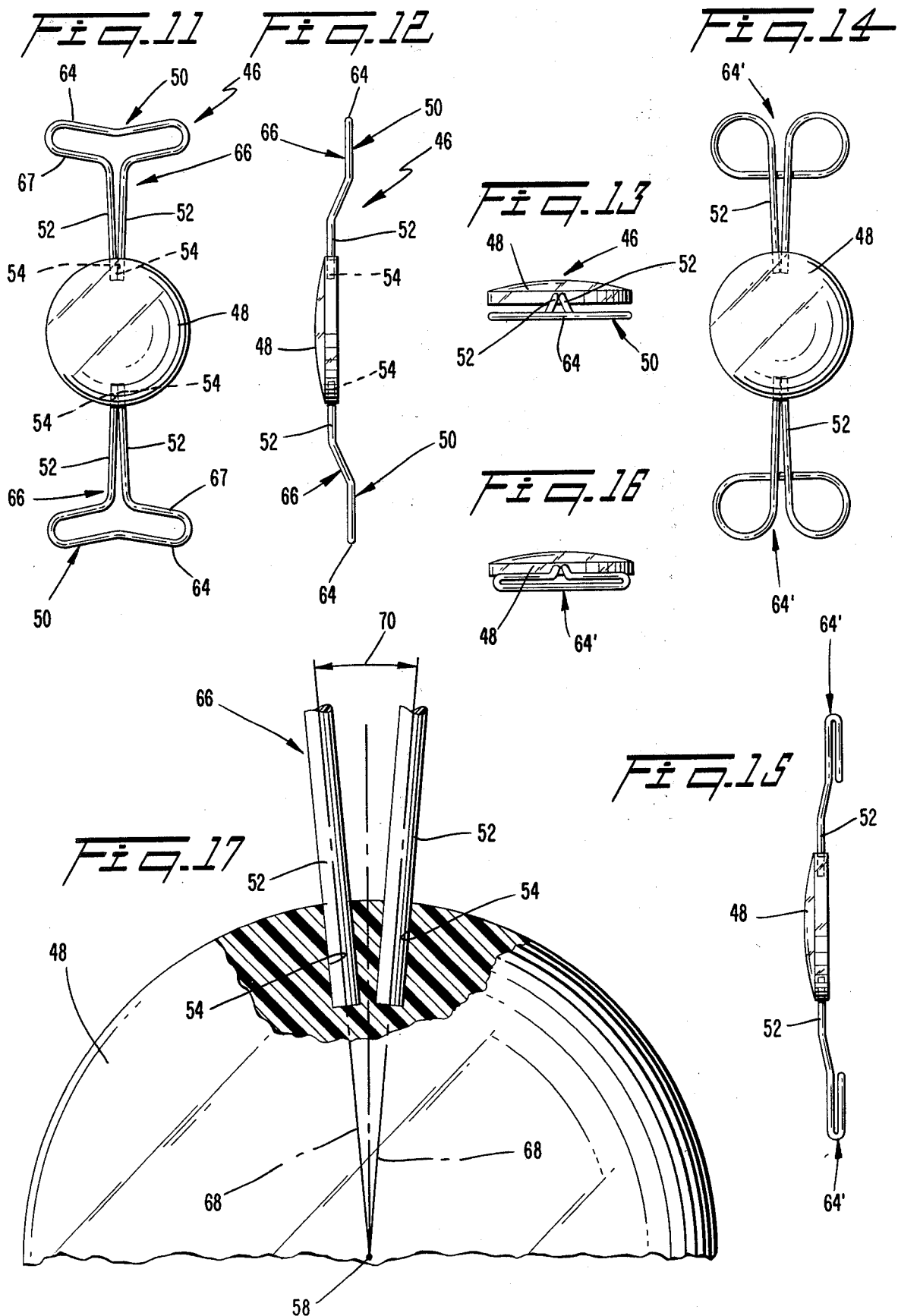

INTRAOCULAR LENS

BACKGROUND OF THE INVENTION

The present invention relates to intraocular lenses and, more particularly, to anterior chamber intraocular lenses having support haptics of filament material.

The field of intraocular lenses is fairly new, dating back to approximately 1948 when Dr. Harold Ridley of England first implanted a disc of plastic in the posterior chamber of the eye behind the iris in the former site of the crystalline lens which had been removed because of a cataractous condition. From that beginning, several major schools of lens design emerged. One of the earliest was the anterior chamber lens, such as that generally indicated as 10 in FIGS. 1 and 2. The particular design shown in simplified form as 10 in FIGS. 1 and 2 was originated by Dr. Strampelli of Italy and later made popular by Dr. Peter Choyce of England. The basic design has undergone several modifications, but is still in popular use today. Lens 10 is in the form of a rigid strip or ribbon of polymethylmethacrylate plastic 12 into which a lens portion 14 is formed at the center. Opposite ends of the strip 12 have feet 16 formed therein. The lens is placed within the anterior chamber 18 with the feet 16 disposed in the angle 20 where the iris meets the cornea 24.

There are several problems associated with rigid, platelike anterior chamber lenses. These include a lack of any longitudinal compressibility such that the diameter of the eye must be carefully measured and an attempt made to insert a lens 10 of the proper length for the specific eye. If the lens is too short, it may come free and contact the delicate endothelium lining the cornea 24. If the lens is too long, the feet 16 can press into the delicate tissue of the eye, and in particular, into the blood vessels which abound in the area, with the possibility of rupture thereof as well as a condition known as "tender eye" which can manifest itself as anything from severe pain to the constant feeling of having "something in the eye."

To prevent the iris 22 from rubbing on the strip 12, it is typical to "vault" the strip 12 as shown in side view in FIG. 2. That is, the strip 12 is not in a single plane, but curves slightly away from the iris 22 in the center. Additionally, such lenses require very careful edge polishing to prevent sharp edges which can damage delicate tissue.

It is preferred to have any implanted lens as light as possible and, as can be seen, the lens 10 of FIGS. 1 and 2 has much surplus material in the strip 12 which can be eliminated. Starting with the basic lens 10 of FIGS. 1 and 2, many designs have been created by eliminating various portions of strip 12. Lenses 26 through 34 of FIGS. 3 through 7, respectively, show some of the variations created by eliminating excess material from such a lens. Note that in all the designs, the feet 16 are integral with the lens portion 14 by virtue of a web of plastic interconnecting the two. Yet another variation (not shown) reverses the curvature of the portion containing feet 16 into a curve approximating the curve of the angle 20. Because of its similar shape, such a configuration is referred to as an "anchor" lens.

As can be imagined, lenses such as those of FIGS. 3 through 7 are even more difficult to polish than the basic shape of FIGS. 1 and 2.

From the very beginning, attempts were made to eliminate many of the foregoing problems by substituting filament material for the so-called "haptic" portion which supports the lens portion 14. Because of its ready availability and ability to be sterilized, standard suture material came to be commonly applied to such use. One of the earliest of such lenses was that of Dannheim which is indicated generally as 36 in FIG. 8. The Dannheim lens 36 had a lens body 38 having a pair of parallel bores 40 therethrough through which a continuous strand of suture material 42 was passed to form two opposed closed loops 44. It was Dr. Dannheim's belief that the lens 36 as thus constructed would adapt to varying diameters of the eye and provide a compressible lens. Unfortunately, it is typical of a looped configuration such as that of lens 36 that when the loops 44 are subjected to a longitudinal compressive force, rather than bulging outward at the side individually to foreshorten the overall length of the lens 36 in the plane of the lens body, the combined loop 44 and lens body 38 will tend to bow forward or backward in a direction normal to the surface of the lens body 38. When placed in the position shown in FIG. 2, the Dannheim lens 36 may bow back allowing the iris to rub against the lens or bow forward toward the endothelium lining the cornea 24. The smaller the diameter of the eye into which the lens was placed, the more pronounced the bowing. As a result, the lens body 38 could be placed undesirably close to the endothelium lining the cornea 24, and being effectively a spring-mounted mass, the lens body 38 might bounce against the endothelium.

Dr. Barraquer of Spain modified the Dannheim lens 36 by clipping each of the loops 44 to form a pair of opposed open loops. This eliminated the bowing problem, as he had hoped, but, unfortunately, resulted in the overall rigidity of his lens being insufficient to maintain the lens body in a stable position. After the implantation of a few lenses with unacceptable results, Dr. Barraquer ceased implantations of that design.

Wherefore, it is the object of the present invention to provide a non-rigid compressible anterior chamber lens having the benefits of a filament-type support haptic such as ease of manufacture, lightness, and smooth extruded haptics which do not require polishing, while having more desirable characteristics than prior lenses of a smiliar type.

SUMMARY

The foregoing objectives are achieved in an intraocular lens in which a plastic lens body is supported on opposite sides by special suture loops. The loops are formed of smooth extruded plastic strand material and closed by connection of the two inner free ends in the body and opening out of the edge of the body receiving the free ends and being disposed on radius lines passing through the optical center of the lens body and subtending an angle of from 2° to 10°. The haptic supports each have inner and outer portions which are preferably substantially parallel to each other but interconnected by inclined portions whereby longitudinal compression tends to be mostly absorbed in the supports with minimum forward displacement of the lens body, the configuration avoiding backward displacement of the lens body toward the iris.

Preferably, the strands of the haptic support have a diameter of at least 0.23 millimeters so as to provide the degree of rigidity desired to maintain the lens in position.

DESCRIPTION OF THE DRAWINGS

FIG. 1 is a front elevation showing a prior art anterior chamber lens in front elevation view.

FIG. 2 is a cutaway side elevation through the area adjacent the iris of an eye and with cornea broken away and showing the lens of FIG. 2 in side elevation.

FIGS. 3–7 show variations of the lens of FIGS. 1 and 2 created by eliminating unnecessary portions, leaving only the required portions connected together by a web of support material at various locations.

FIG. 8 is a front elevation of a prior art lens having closed loops of filament material.

FIG. 9 is an elevation view of an iris when restricting the size of the pupillary opening.

FIG. 10 is a front elevation of an iris showing the movement during enlargement of the pupillary opening.

FIG. 11 is a front elevation of a lens according to the present invention in the preferred embodiment.

FIG. 12 is a side elevation view of the lens of FIG. 11.

FIG. 13 is an end elevation of the lens of FIG. 11.

FIG. 14 is a front elevation of a lens according to the present invention in an alternate embodiment thereof.

FIG. 15 is a side elevation of the lens of FIG. 14.

FIG. 16 is an end elevation of the lens of FIG. 15.

FIG. 17 is an enlarged view of a lens body showing the method of mounting the haptic strands thereto according to the teaching of the present invention.

DESCRIPTION OF THE PREFERRED AND ALTERNATE EMBODIMENT

With reference to FIGS. 11 through 15, the lens of the present invention in its preferred embodiment is generally indicated as 46. Lens 46 comprises a polished plastic lens body 48 having a pair of filament loop type haptic support structures 50 disposed in opposed relationship with the substantially straight free ends 52 of each structure 50 disposed within bores 54 in the edge of lens body 48. The free ends 52 are held within bores 54 by a well-known process in the art referred to as "staking" which forms no particular part of the present invention.

It is preferred to have the haptic support structures 50 be of extruded polypropylene plastic, although it is conceived that the same benefits could be achieved through the use of extruded polymethylethacrylate, which is becoming more common in usage at the present time. To help achieve a desired stability of the lens, it is preferred that the strands of the haptic support structures 50 be of so-called "3-0" suture material which is, in fact, about 0.23 millimeters in diameter. Contrary to earlier designs employing strand material of a lighter nature (i.e. with a thinner diameter and, therefore, more flexible), this size coupled with the configuration to be described in greater detail hereinafter provides a better balance of rigidity and compressibility to resist undesirable deformation while allowing some compression in the longitudinal direction, so as to accommodate slight variations in overall length with a substantially lesser anterior displacement of the lens body. In the preferred form, the anterior displacement of the lens body is approximately one half of the overall longitudinal compression of the lens over the range of compressive forces of importance in vivo.

As can be seen in the side elevation of FIG. 12 and the end elevation of FIG. 13, it is preferred that the haptic support structures 50 be configured to provide a vault to the overall lens to help minimize the risk of iris chafing and pupillary capture of the lens body. Preferably, the vault is substantially 0.6 mm.

Turning temporarily to FIGS. 9 and 10, FIG. 9 shows the movement of the tissue of the iris 22 during restriction of the size of the pupillary opening 56. It is characteristic of the tissue of the iris that the tissue moves radially inward toward the optic center of the eye 58, as symbolized by the arrows 60. Similarly, in FIG. 10, the arrows 62 symbolize the movement of the tissue about the periphery of the pupillary opening 56 moving radially outward away from the optic center as the pupil dilates to increase the size of the pupillary opening. This movement of the tissue of the iris seems to have been unacknowledged in the construction of intraocular lenses which do or can come into contact with this moving tissue. The tissue of the iris could be described as light and billowy, as opposed to being dense, such that if the characteristics of the tissue itself and the directions of movement are not accounted for in the lens structure and implantation, a condition known as "iris chafing" can occur. In such a state, the moving tissue of the iris 22 rubs on an edge or surface of or can catch against the lens itself thereby restricting its movement.

With the foregoing in mind, an objective of the invention is to provide a desirable type of haptic structure which reacts properly under longitudinal compression and which has reduced potential for "iris chafing." In the lens of the invention bowing occurs within each haptic support and such bowing produces minimum anterior displacement of the lens body if a proper lens size has been selected. The surgeon must select the proper lens diameter using a "white to white" or anterior chamber "dip stick" technique. The inner ends of the haptic structure are on radii of the lens body to avoid iris chafing.

Referring first to FIG. 11, each haptic support structure 50 has an outer horizontal portion 64 and a resiliently flexible strut portion 66 including inner ends 52 interconnecting the lens body 48 to the horizontal portion 64. An important feature of the present invention is shown enlarged in FIG. 17 wherein bores 54 for the free ends 52 are disposed along center lines 68 which are, in fact, radius lines extending through the optic center 58 of lens body 48. The bores may even touch at their inner ends. The center lines 68 subtend an angle as indicated by the arrow 70 preferably of about 2° but up to as large as 10°. This configuration provides two major features. First, since the straight inner portions 52 of the support structure strut portions 66 lie along radius lines (center lines 68), the iris 22 in moving as described with reference to FIGS. 9 and 10 moves parallel with them rather than at an angle to them. This reduces the potential for undesired chafing of the iris. Additionally, the inclined sections 67 of the strut portion 66 provide a degree of controlled flexure when compressive forces are applied from the horizontal portions 64. Such forces tend to cause bending at the corners where the inclined portions 67 join the straight portions 52 and this tends to cause both sets of portions 52 and the lens body 48 to be displaced outwardly as a unit to a position parallel to their previous position. In the preferred configuration of FIGS. 11 and 12, the lens body is displaced approximately one unit for two units of longitudinal compression in diameter of the lens. The unique vaulting provided by the haptic supports 50 tends therefore to be under control with the displacement outward, small, and parallel. However, while the lens 46 of the present invention will accommodate minor differences in diameter, it is not a lens in which "one size fits all."

Turning now to FIGS. 14–16, an alternate embodiment of the present invention is shown. The only difference lies in the configuration of the outer horizontal portion 64. As can be seen, the horizontal portion 64 of the preferred embodiment is shaped like a pair of wings extending outward with respect to the straight portions 52 to form virtual feet at the extremities of the struts. By contrast, the horizontal portion 64' and the embodiment of FIGS. 14–16 is folded back upon itself in what might be referred to as a half-four-leaf-cover arrangement. By so doing, the virtual feet are more pronounced and rounded.

The design aspects of the haptic support structures in both embodiments are the subject of the copending design applications Ser. Nos. 146,678 and 146,679, filed May 5, 1980.

While it is believed that the lens structure described herein has advantageous features not found in previous intraocular lenses, surgical skill remains important in their selection, and implantation as well as in the selection of patients to receive implantation.

Modifications may be made without departing from the spirit and scope of the invention.

Having thus described my invention, I claim:

1. In an intraocular lens having a plastic lens body with a pair of opposed haptic supports of strand material extending radially outward substantially in the plane of the lens body, the improvement comprising:

each haptic support is divided into a horizontal portion for contacting the periphery of the space in the eye where placed and a resiliently flexible strut portion connecting the lens body to said horizontal portion, said strut portion comprising a pair of strands disposed on radius lines passing through the optical center of the lens body and subtending an angle of from 2° to 10°.

2. An intraocular lens for placement across the anterior chamber of an eye comprising:
(a) a lens body; and,
(b) a pair of opposed haptic members carried by said lens body and extending radially outward therefrom substantially in the plane of said lens body, each haptic member being of strand material at least 0.23 millimeters in diameter and comprising two close-adjacent strand portions adjacent said lens body forming a strut portion and the remaining strand portion between said strand portions forming said strut being disposed transverse the end of said strut and adapted to lie in the edge of the anterior chamber, said strand portions forming said strut being disposed on radius lines passing through the optic center of said lens body and subtending an angle of from 2° to 10°.

3. An intraocular lens for implantation across the anterior chamber of an eye comprising a lens body and a pair of diametrically opposed haptic supports extending radially outwardly from opposite sides of the lens body, each support comprising a reversely turned, smooth resilient plastic suture filament having two free ends at its inner radial portion connected to the lens body, said free ends being substantially straight and spaced closely together, said suture filament having a foot formed therein at its outer radial portion and said foot being substantially wider than said free ends, said suture filament having a strut portion interconnecting said free ends and said foot and serving to support said foot so that it is substantially parallel to but displaced along the lens axis from the plane of said free ends to provide a vault for the lens, said free end portions being substantially straight and said strut portions including portions inclined rearwardly away from said straight free end portion to space said foot rearwardly from the inner portion and provide a controlled locale or bending due to compressive forces on the foot, said strut portion providing the lens body and straight free ends be displaced outwardly substantially as a unit in an amount about one-half of the amount of axial compression in diameter of the lens, said lens body having bores therein opening out of the outer edge thereof, said straight free ends of said future filament extending in said bores, said bores and free end extending along converging radius lines of between 2° and 10° passing substantially through the optical center of the lens body.

* * * * *

UNITED STATES PATENT AND TRADEMARK OFFICE
CERTIFICATE OF CORRECTION

PATENT NO. : 4,442,553
DATED : April 17, 1984
INVENTOR(S) : Philip C. Hessburg, M.D.

It is certified that error appears in the above-identified patent and that said Letters Patent are hereby corrected as shown below:

Column 5, Line 12:

The word "cover" should be --clover--.

Claim 3, Line 32:

The word "or" should be --for--.

Signed and Sealed this

Twenty-first Day of August 1984

[SEAL]

Attest:

GERALD J. MOSSINGHOFF

Attesting Officer

Commissioner of Patents and Trademarks